United States Patent
Boulens et al.

(10) Patent No.: US 9,283,554 B2
(45) Date of Patent: Mar. 15, 2016

(54) NICKEL-BASED CATALYTIC COMPOSITION, AND ITS USE IN A PROCESS FOR THE OLIGOMERIZATION OF OLEFINS

(71) Applicants: IFP Energies nouvelles, Rueil-Maimaison (FR); UNIVERSITEIT VAN AMSTERDAM, Amsterdam (NL)

(72) Inventors: Pierre Boulens, Lyons (FR); Pierre-Alain Breuil, Lyons (FR); Joost Reek, Amersfoort (NL); Helene Olivier-Bourbigou, Saint Genis-Laval (FR)

(73) Assignees: IFP Energies Nouvelles, Rueil-Malmaison (FR); Universiteit Van Amsterdam, Amsterdam (NL)

( * ) Notice: Subject to any disclaimer, the term of this patent is extended or adjusted under 35 U.S.C. 154(b) by 0 days.

(21) Appl. No.: 14/694,052

(22) Filed: Apr. 23, 2015

(65) Prior Publication Data

US 2015/0306588 A1 Oct. 29, 2015

(30) Foreign Application Priority Data

Apr. 28, 2014 (FR) .................................. 14 53816

(51) Int. Cl.
| | | |
|---|---|---|
| C07F 15/00 | (2006.01) | |
| B01J 31/00 | (2006.01) | |
| C07C 2/02 | (2006.01) | |
| B01J 31/18 | (2006.01) | |
| C07C 2/32 | (2006.01) | |
| C07F 15/04 | (2006.01) | |
| B01J 31/14 | (2006.01) | |
| B01J 31/02 | (2006.01) | |
| B01J 31/22 | (2006.01) | |

(52) U.S. Cl.
CPC .......... *B01J 31/1845* (2013.01); *B01J 31/0267* (2013.01); *B01J 31/143* (2013.01); *B01J 31/2247* (2013.01); *C07C 2/32* (2013.01); *C07F 15/045* (2013.01); *B01J 2231/20* (2013.01); *B01J 2531/0213* (2013.01); *B01J 2531/847* (2013.01); *C07C 2531/18* (2013.01)

(58) Field of Classification Search
CPC ............... B01J 31/1845; B01J 31/0267; B01J 31/2247; B01J 31/143; B01J 2231/20; B01J 2531/0213; B01J 2531/847; C07C 2/32; C07C 2531/18; C07F 15/045
USPC ........................ 556/20, 21; 502/117; 585/523
See application file for complete search history.

(56) References Cited

U.S. PATENT DOCUMENTS

| | | | |
|---|---|---|---|
| 3,676,523 | A | 7/1972 | Mason |
| 6,060,569 | A | 5/2000 | Bennett et al. |
| 8,283,276 | B2 | 10/2012 | Reek et al. |
| 2011/0003959 | A1 | 1/2011 | Reek et al. |

FOREIGN PATENT DOCUMENTS

EP 2062906 A1 5/2009

OTHER PUBLICATIONS

Search Report dated Jan. 14, 2015 issued in corresponding FR 1453816 application (pp. 1-3).
Frederic W. Patureau, et al., "Synthesis, Coordination Chemistry, and Cooperative Activation of H 2 with Ruthenium Complexes of Proton-Responsive METAMORPhos Ligands", European Journal of Inorganic Chemistry, vol. 2014, No. 10 (2014) pp. 1826-1835.
Frederic W. Patureau, et al., "Supramolecular Hydrogen-Bonding Tautomeric Sulfonamido-Phosphinamides: A Perfect P-Chirogenic Memory", European Journal of Inorganic Chemistry, vol. 2012, No. 3 (2012) pp. 496-503.

*Primary Examiner* — Porfirio Nazario Gonzalez
(74) *Attorney, Agent, or Firm* — Millen, White, Zelano & Branigan, P.C.

(57) ABSTRACT

The invention describes a nickel-based composition. The invention also concerns the use of said composition as a catalytic composition in an olefin oligomerization process.

20 Claims, No Drawings

NICKEL-BASED CATALYTIC COMPOSITION, AND ITS USE IN A PROCESS FOR THE OLIGOMERIZATION OF OLEFINS

The present invention relates to a novel nickel-based composition. The invention also relates to the use of said composition as a catalyst for chemical transformation reactions.

PRIOR ART

The preparation of catalytic compositions based on transition metals for application thereof in various fields of chemistry is known, in particular in the field of catalytic transformations such as hydroformylation, hydrogenation, cross-coupling, olefin oligomerization, etc.

The preparation of catalytic compositions of this type depends on the choice of metal and on appropriate ligands. Among these ligands, bidentate ligands represent an important class of ligands used in the preparation of catalytic compositions based on transition metals for various types of catalytic transformations.

The document EP 2 220 099 B1 describes a system of coordination complexes comprising multidentate ligands with formula: $R_1$—$SO_2$—NH—$P(XR_2)_2$; or $R_1$—$SO_2$—N=PH$(XR_2)_2$, or $R_1$—SO(OH)=NP$(XR_2)_2$, in which X is independently O, S, NH, or a bond; in which $R_1$ and $R_2$ are independently selected from an alkyl group, which may or may not be substituted, and an aryl group, in which at least one equivalent of ligand is complexed with one equivalent of a metal selected from rhodium, iridium, the platinum, palladium and the lanthanides. EP 2 220 099 B1 indicates that the coordination complex system may be used as a catalyst for hydroformylation, hydrogenation, polymerisation, isomerisation etc.

In its research, the Applicant has developed a novel nickel-based composition. Surprisingly, it has been shown that such compositions have interesting catalytic properties. In particular, these compositions have a good catalytic activity in the oligomerization of olefins, more precisely in the dimerization of ethylene to form 1-butene.

One aim of the invention is to provide a novel nickel-based composition. In another aspect, a novel catalytic system is proposed comprising said composition for chemical transformation reactions, in particular for the oligomerization of olefins.

DETAILED DESCRIPTION OF THE INVENTION

Composition of the Invention

The catalytic composition of the invention comprises:
at least one precursor of nickel with an oxidation number of (0) or (+II),
at least one ligand with formula 1a), 1b) or 1c)

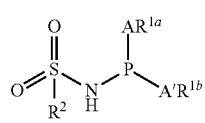

1a)

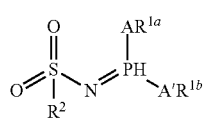

1b)

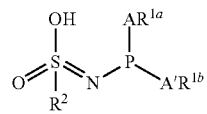

1c)

in which
A and A', which may be identical or different, are independently O, S, $NR^3$ or a single bond between the phosphorus atom and a carbon atom,
the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements,
the groups $R^1$, represented in the formula by $R^{1a}$ and $R^{1b}$, with $R^{1a}$ and $R^{1b}$ being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements,
the group $R^2$ is selected from alkyl groups which may or may not be cyclic, which may or may not be substituted and which may or may not contain heteroelements, and aromatic groups which may or may not be substituted and which may or may not contain heteroelements, with the condition that when a precursor of nickel with an oxidation number of (+II) is used in the composition, it is used in the presence of a reducing agent or in the presence of a Brönsted base.

In the context of the present invention, the term "alkyl" is intended to mean a linear or branched hydrocarbon chain containing 1 to 15 carbon atoms, preferably 1 to 10. Preferred alkyl groups are advantageously selected from methyl, ethyl, propyl, isopropyl, butyl, isobutyl and tert-butyl groups. These alkyl groups may be substituted with heteroelements or groups containing heteroelements, such as a halogen or an alkoxy group. The term "alkoxy" substituent means an alkyl-O— group in which the term "alkyl" has the meaning given above. preferred examples of alkoxy substituents are methoxy or ethoxy groups.

The term "cyclic alkyl" means a monocyclic hydrocarbon group containing more than 3 carbon atoms, preferably 4 to 24, more preferably 6 to 12, preferably a cyclopentyl, cyclohexyl, cyclooctyl or cyclododecyl group, or a polycyclic (bi- or tricyclic) group containing more than 3 carbon atoms, preferably 4 to 18, such as adamantyl or norbornyl groups, for example.

The term "linear unsaturated alkyl" or "cyclic unsaturated alkyl" means a linear or cyclic alkyl group containing at least one unsaturated bond, the term "alkyl" and "cyclic alkyl" having the meaning given above.

The term "aromatic" means a mono- or polycylic aromatic group, preferably mono- or bicyclic, containing 5 to 20 carbon atoms. When the group is polycyclic, i.e. it comprises more than one cyclic ring, the cyclic rings may advantageously be condensed in pairs or connected in pairs via σ bonds. The aromatic group in accordance with the invention may contain a heteroelement such as nitrogen, oxygen or sulphur.

The term "ligand" as used in the present invention is used indiscriminately to mean one or more of the limiting forms with formula 1a), 1b) and/or 1c) used to form the composition of the invention.

The two groups $R^1$ ($R^{1a}$ and $R^{1b}$) may be mutually identical or different. These two groups $R^{1a}$ and $R^{1b}$ may also be bonded together. In such a case, the two groups $R^{1a}$ and $R^{1b}$ may correspond to groups such as bis-phenyl or bis-naphthyl.

The ligands of the invention may be prepared by a condensation reaction of a sulphonamide, for example para-n-butylphenyl sulphonamide, and a phosphine halide such as $Ph_2PCl$, in the presence of a Brönsted base such as triethylamine, for example, in a solvent. In solution, these ligands may (co)exist in the three forms 1a), 1b) or 1c) described above.

The composition of the invention may also comprise an additional Lewis base. In the context of the present invention, the term "Lewis base" means any chemical entity a constituent of which has one or more free or non-bonding electron pairs. The Lewis bases of the invention in particular correspond to any ligand comprising an oxygen, nitrogen or phosphorus atom with a free or non-bonding electron pair or a $\pi$ double bond which is capable of forming an $\eta^2$ type coordination with the nickel.

The additional Lewis base of the composition of the invention may be a phosphine of the type $p(A^IR'^{1a})(A'^IR'^{1b})(A'''R'^{1c})$ or a phosphinamine of the type $(R'^{1a}A^I)(R'^{1b}A^{I1})P-NH(R'^2)$ or $(R'^{1a}A^I)(R'^{1b}A^{I1})P-NH-S(O)_2(R'^2)$, in which:

$A^I$, $A'^I$ and $A'''^1$, which may be mutually identical or different, are independently O, S, $NR^3$, or a single bond between the phosphorus atom and a carbon atom, the group $R^3$ is either a hydrogen atom or an alkyl group, which may or may not be cyclic, which may or may not be substituted and which may or may not contain heteroelements, or an aromatic group which may or may not be substituted and which may or may not contain heteroelements, the groups $R'^1$, i.e. $R'^{1a}$, $R'^{1b}$, and $R'^{1c}$, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements, the group $R'^2$ is selected from alkyl groups which may or may not be cyclic, which may or may not be substituted and which may or may not contain heteroelements, and aromatic groups which may or may not be substituted and which may or may not contain heteroelements.

In accordance with the invention, the groups $R^1$ i.e. $R^{1a}$ and $R^{1b}$, which may be identical or different and which may or may not be bonded together, and the groups $R'^1$, i.e. $R'^{1a}$, $R'^{1b}$ and $R'^{1c}$, which may be identical or different and which may or may not be bonded together, are independently selected from alkyl groups containing 1 to 15 carbon atoms and aromatic groups containing 5 to 20 carbon atoms, which may or may not be substituted and which may or may not contain heteroelements.

Preferably, the groups $R^1$, i.e. $R^{1a}$ and $R^{1b}$ which may be identical or different, which may or may not be bonded together, and the groups $R'^1$, i.e. $R'^{1a}$, $R'^{1b}$ and $R'^{1c}$, which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not be substituted and which may or may not contain heteroelements. In the case in which the groups $R^1$, i.e. $R^{1a}$ and $R^{1b}$, which may be identical or different, are bonded together, these groups may correspond to groups such as bis-phenyl or bis-naphthyl. In the case in which the groups $R'^1$, which may be identical or different, are bonded together, these groups may correspond to groups such as bis-phenyl or bis-naphthyl.

In accordance with the invention, the groups $R^2$ and the groups $R'^2$, which may be identical or different, are independently selected from alkyl groups containing 1 to 15 carbon atoms and aromatic groups containing 5 to 20 carbon atoms, which may or may not be substituted and which may or may not contain heteroelements.

Preferably, the groups $R^2$ and the groups $R'^2$, which may be identical or different, are independently selected from methyl, trifluoromethyl, ethyl, n-propyl, i-propyl, n-butyl, i-butyl, t-butyl, pentyl, cyclohexyl and adamantyl groups, which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain heteroelements.

Preferably, the group $R^3$ is either a hydrogen atom or an alkyl group.

The compositions of the invention may or may not be in the presence of a solvent. It is possible to use a solvent selected from organic solvents, in particular from ethers, alcohols, chlorine-containing solvents and saturated, unsaturated, aromatic or non-aromatic, cyclic or non-cyclic hydrocarbons. Preferably, the solvent is selected from hexane, cyclohexane, methylcyclohexane, heptane, butane or isobutane, monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol, ethanol, pure or as a mixture, and ionic liquids. In the case in which the solvent is an ionic liquid, it is advantageously selected from the ionic liquids described in U.S. Pat. No. 6,951,831 B2 and FR 2 895 406 B1.

When the nickel precursor has oxidation number (0), it may be selected from nickel(0)bis(cycloocta-1,5-diene), nickel(0)bis(cycloocta-1,3-diene), nickel(0)bis(cyclooctatetraene), nickel(0)bis(cycloocta-1,3,7-triene), bis(o-tolylphosphito) nickel(0) (ethylene), nickel(0)tetrakis(triphenylphosphite), nickel(0)tetrakis(triphenylphosphine) and nickel(0)bis(ethylene), used alone or as a mixture. Said nickel precursors may optionally be complexed with Lewis bases.

When the nickel precursor has oxidation number (+II), it may be selected from nickel (II) chloride, nickel(dimethoxyethane) chloride(II), nickel(II) bromide, nickel(II) (dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel(II) phenates, nickel(II) acetate, nickel(II) trifluoroacetate, nickel(II) triflate, nickel(II) acetylacetonate, nickel(II) hexafluoroacetylacetonate, allylnickel(II) chloride, allylnickel(II) bromide, methallylnickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, used alone or as a mixture. Said nickel precursors may optionally be complexed with Lewis bases.

When a nickel precursor with an oxidation number of (+II) is used in the composition, it is used in the presence of a reducing agent or in the presence of a Brönsted base.

It is possible to use any agent which results in the reduction of nickel which is known to the skilled person. The reducing agent may be selected from $NaBH_4$, $LiAlH_4$, $AlEt_3$, Na, K, $KC_8$ and dihydrogen.

Any Brönsted base which is known to the skilled person may be used. The term "Brönsted base" means any molecular entity or corresponding chemical species which is capable of accepting a proton, such as triethylamine, for example.

In accordance with the invention, the molar ratio between the ligand or ligands with formula 1a), 1b) or 1c) and the nickel precursor is advantageously in the range 0.05 to 10, preferably in the range 0.5 to 3.

In accordance with the invention, the molar ratio between the Lewis base and the nickel precursor is advantageously in the range 0.05 to 10, preferably in the range 0.5 to 3.

A non-exhaustive list of ligands which may be suitable for the preparation of the compositions of the invention is represented below. The ligands here are represented in their limiting forms 1a) and 1b).

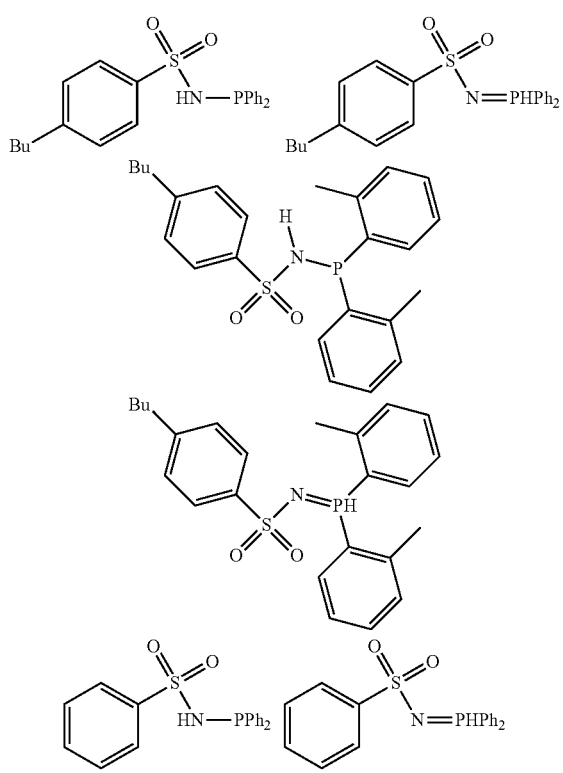

-continued

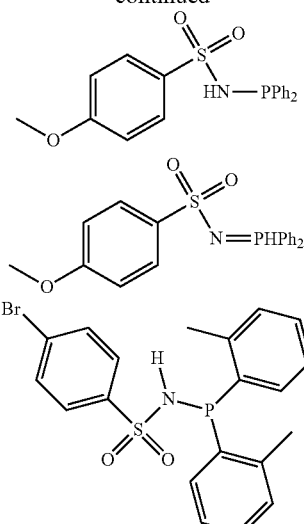

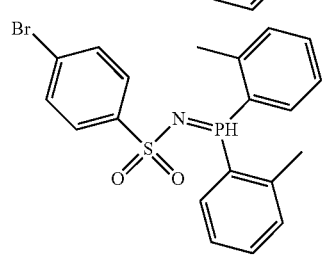

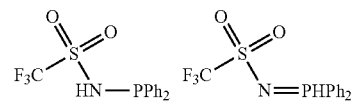

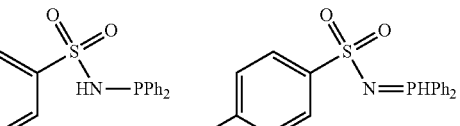

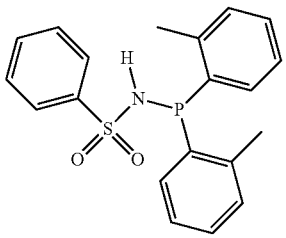

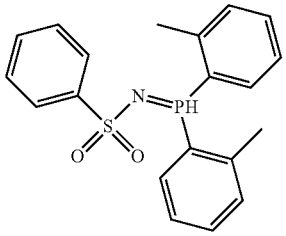

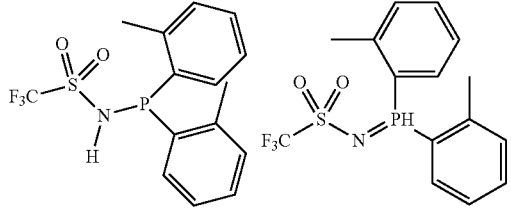

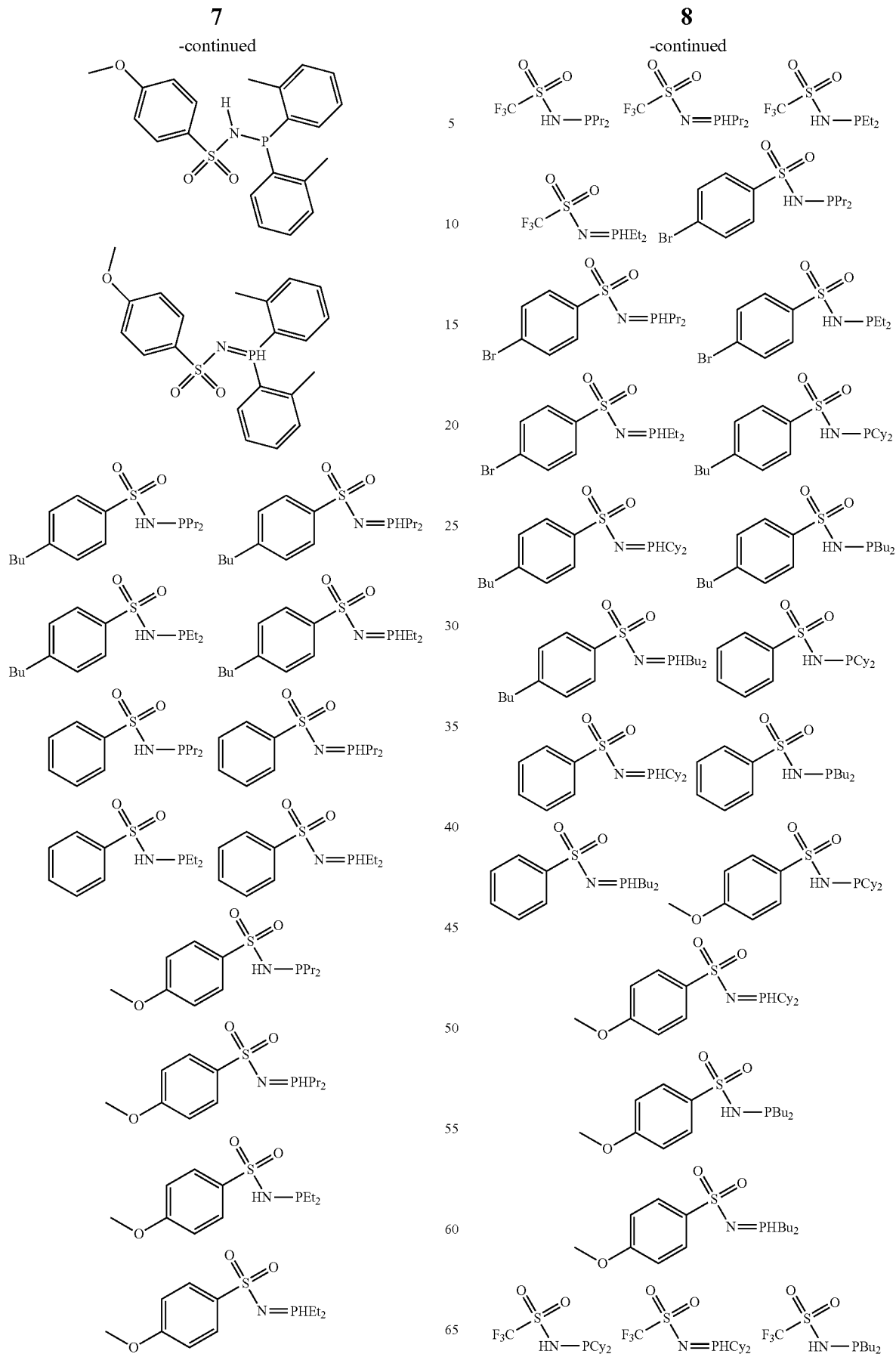

-continued

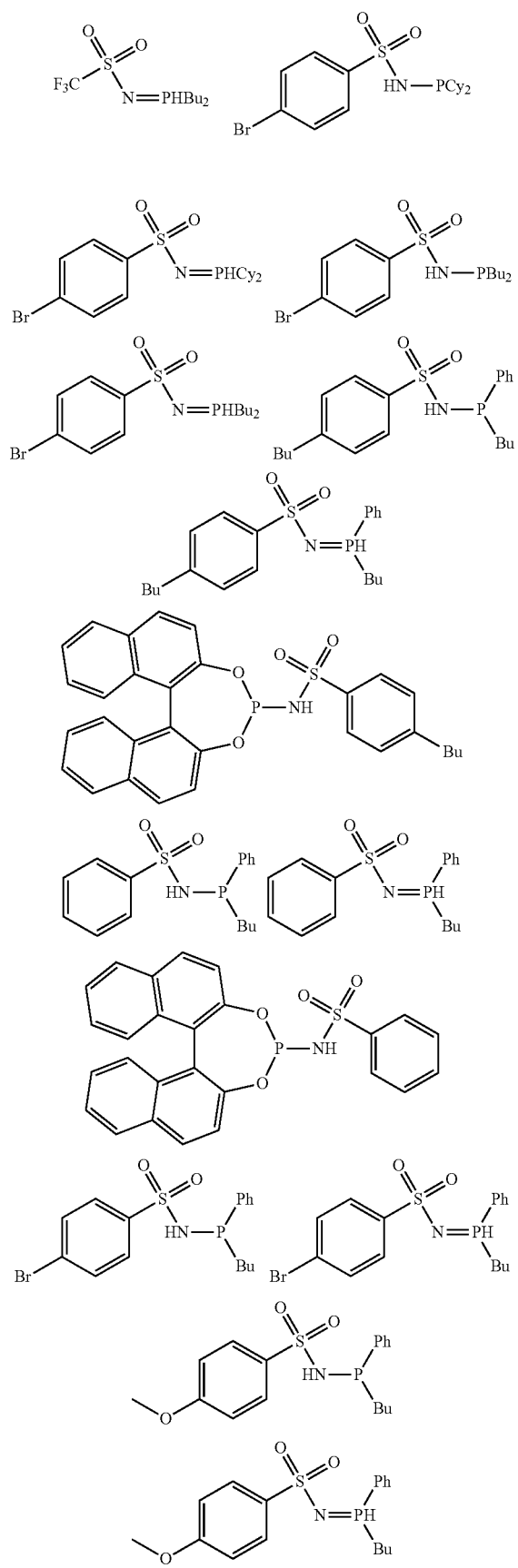

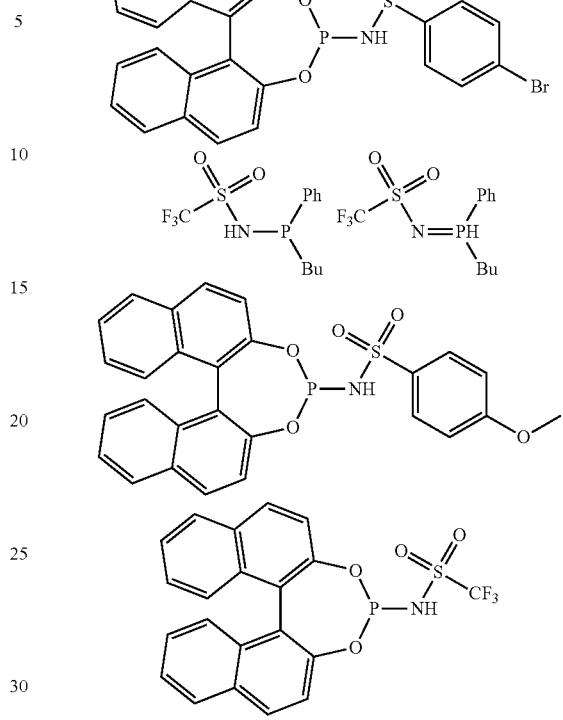

Use of the Composition of the Invention

The compositions of the invention may be used as a catalyst in a chemical transformation reaction such as a hydrogenation, hydroformylation, cross coupling or olefin oligomerization reaction. In particular, these complexes are used in a process for the oligomerization of a feed of olefins advantageously containing 2 to 10 carbon atoms.

Preferably, the oligomerization process is a process for the dimerization of ethylene to 1-butene.

The compositions of the invention may also comprise a compound known as an activating agent. Said activating agent is advantageously selected from the group formed by tris(hydrocarbyl)aluminium compounds, chlorine-containing or bromine-containing hydrocarbylaluminium compounds, aluminium halides, aluminoxanes, organo-boron compounds, and organic compounds which are capable of donating or accepting a proton, used alone or as a mixture.

The tris(hydrocarbyl)aluminium compounds, the chlorine-containing or bromine-containing hydrocarbylaluminium compounds and the aluminium halides preferably have the general formula $Al_xR_yW_z$, in which R represents a monovalent hydrocarbon radical containing, for example, up to 12 carbon atoms such as alkyl, aryl, aralkyl, alkaryl or cycloalkyl, W represents a halogen atom selected from chlorine and bromine, for example, W preferably being a chlorine atom, x takes the value of 1 to 2, y and z taking a value of 0 to 3. Examples of compounds of this type which may be mentioned are ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$).

In the case in which said activating agent is selected from aluminoxanes, said activating agent is advantageously selected from methylaluminoxane (MAO), ethylaluminoxane and modified methylaluminoxanes (MMAO). These activating agents may be used alone or as a mixture.

Preferably, said activating agent C is selected from dichloroethylaluminium (EtAlCl$_2$) and methylaluminoxane (MAO).

In the case in which said activating agent is selected from organoboron compounds, said activating agent is preferably selected from Lewis acids of the tris(aryl)borane type, such as tris(perfluorophenyl)borane, tris(3,5-bis(trifluoromethyl)phenyl)borane, tris(2,3,4,6-tetrafluorophenyl)borane, tris(perfluoronaphtyl)borane, tris(perfluorobiphenyl)borane and their derivatives and (aryl)borates associated with a triphenylcarbenium cation, or a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

In the case in which said activating agent is selected from organic compounds which are susceptible of donating a proton, said activating agent is preferably selected from acids with formula HY in which Y represents an anion.

In the case in which said activating agent is selected from organic compounds which are susceptible of accepting a proton, said activating agent is preferably selected from Brönsted bases.

The solvent for the oligomerization process may be selected from organic solvents, preferably from ethers, alcohols, chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, dichloromethane, chlorobenzene, methanol and ethanol, pure or as a mixture, and ionic liquids. In the case in which said reaction solvent is an ionic liquid, it is advantageously selected from the ionic liquids described in U.S. Pat. No. 6,951,831 B2 and FR 2 895 406 B1.

Oligomerization is defined as the transformation of a monomer unit into a compound or mixture of compounds with general formula $C_pH_{2p}$, with $4 \leq p \leq 80$, preferably with $4 \leq p \leq 50$, more preferably with $4 \leq p \leq 26$ and highly preferably with $4 \leq p \leq 14$.

The olefins used in the oligomerization process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) such as those found in "cuts" obtained from oil refining processes such as catalytic cracking or steam cracking.

Preferably, the olefin used in the oligomerization process is ethylene.

Said olefins may be obtained from non-fossil sources such as biomass. As an example, the olefins used in the oligomerization process or dimerization process of the invention may be produced from alcohols, in particular by dehydration of alcohols.

The concentration of nickel in the catalytic solution is advantageously in the range $1 \times 10^{-8}$ to 1 mol/L, and preferably in the range $1 \times 10^{-6}$ to $1 \times 10^{-2}$ mol/L.

The oligomerization process is advantageously operated at a total pressure in the range between atmospheric pressure and 20 MPa, preferably in the range 0.1 to 8 MPa, and at a temperature in the range $-40°$ C. to $+250°$ C., preferably in the range $-20°$ C. to $150°$ C.

The heat generated by the reaction can be eliminated using any means known to the skilled person.

The oligomerization process may be carried out in a closed system, in a semi-open system or continuously, with one or more reaction stages. Vigorous stirring is advantageously carried out to ensure good contact between the reagent or reagents and the catalytic system.

The oligomerization process may be carried out discontinuously. In this case, a selected volume of the solution comprising the composition of the invention is introduced into a reactor provided with the usual stirring, heating and cooling devices.

The oligomerization process may also be carried out in a continuous manner. In this case, the solution comprising the composition of the invention is injected at the same time as the olefin into a reactor stirred using conventional mechanical means or by external recirculation, maintaining the desired temperature.

The catalytic composition is destroyed by any usual means known to the skilled person, then the reaction products as well as the solvent are separated, for example by distillation. The olefin which has not been transformed may be recycled to the reactor.

The process of the invention may be carried out in a reactor with one or more reaction stages in series, the olefinic feed and/or the catalytic composition, having been pre-conditioned, being introduced continuously, either into the first stage or into the first and any other of the stages. At the reactor outlet, the catalytic composition may be deactivated, for example by injecting ammonia and/or an aqueous solution of sodium hydroxide and/or an aqueous solution of sulphuric acid. The unconverted olefins and any alkanes present in the feed are then separated from the oligomers by distillation.

The products of the present process may find an application, for example, as fuel components for automobiles, as feeds in a hydroformylation process for the synthesis of aldehydes and alcohols, as components for the chemicals, pharmaceuticals or perfumery industry and/or as feeds in a metathesis process for the synthesis of propylene, for example.

The following examples illustrate the invention without limiting its scope.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 14/53.816, filed Apr. 28, 2014, are incorporated by reference herein.

Example 1

Synthesis of ligand L1

Ligand L1 was synthesized using the method described in the literature: F. G. Terrade, *Eur. J. Inorg. Chem.* 2014, 1826-1835.

Preparation of Compositions of the Invention

Preparation of Composition C1

Ligand L1 (4-nBu-$C_6H_4$—$SO_2$—NH—$PPh_2$, 22 mg, 40 μmol, 1 eq), trimethylphosphine (1M solution in toluene, 88 μL, 40 μmol, 1 eq.) and Ni(COD)$_2$ (31.8 mg, 40 μmol, 1 eq) were suspended in 10 mL of toluene and stirred for 30 min. Next, 5 mL of this solution (i.e. 20 μmol of Ni) was removed and injected into the reactor.

Preparation of Composition C2

Ligand L1 (4-nBu-$C_6H_4$—$SO_2$—NH—$PPh_2$, 31.8 mg, 80 μmol, 2 eq.) and Ni(COD)$_2$ (11 mg, 40 μmol, 1 eq.) were dissolved in toluene (10 mL) and the mixture was stirred for 30 min. Two experiments were carried out in parallel with two solutions with different compositions of said composition C2, one solution with a concentration of 20 μmol of Ni and another with a concentration of 100 μmol of Ni, being evaluated in a reactor.

Example 2

Oligomerization of Ethylene

The ethylene oligomerization reaction was evaluated with the compositions C1 and C2. The results obtained are reported in Table 1.

The 250 mL reactor was dried under vacuum at 130° C. for 2 hours then pressurized with 0.5 MPa of ethylene. The temperature was dropped to 20° C., then the excess pressure of ethylene was evacuated to obtain 0.1 MPa. The solvent was added (45 mL of toluene) and the internal temperature was set (40° C. or 80° C.). Once the internal temperature had stabilized, a portion of the catalytic composition C1 or the catalytic composition C2 was introduced (20 μmol of Ni or 100 μmol of Ni). Next, the reactor was pressurized with 3 MPa of ethylene. Stirring (1000 rpm) was commenced (t=0). After the pre-set reaction time, the mixture was cooled to 30° C. with stirring, the reactor was depressurized and the liquid and gas phases were analysed by gas phase chromatography (GC).

The productivity ($g_{oligo}/(g_{Ni} \cdot h)$) is expressed as the mass of oligomers produced (in grams) per unit mass of nickel employed per hour.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A composition comprising:
   at least one precursor of nickel with an oxidation number of (0) or (+II),
   at least one ligand with formula 1a), 1b) or 1c)

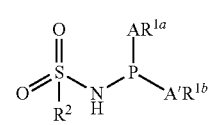

1a)

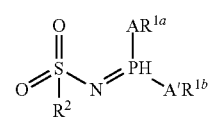

1b)

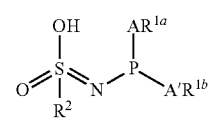

1c)

in which

A and A', which may be identical or different, are independently O, S, $NR^3$ or a single bond between the phosphorus atom and a carbon atom, the group $R^3$ is either a hydrogen atom or an alkyl group, which may or may not be cyclic, which may or may not be substituted and which may or may not contain heteroelements, or an aromatic group, which may or may not be substituted and which may or may not contain heteroelements, the groups $R^{1a}$ and $R^{1b}$ being mutually identical or different and which may or may not be bonded together, are selected from alkyl groups which may or may not be cyclic, which may or may not be substituted and which

TABLE 1

Oligomerization of ethylene with compositions C1 and C2.

| Composition | Temperature (° C.) | Quantity of catalyst (μmol) | Mass of oligomers (g) | Reaction time (min) | Productivity $g_{oligo}/(g_{Ni} \cdot h)$ | Distribution of products (by wt)[a] | | | 1-C4[b] |
|---|---|---|---|---|---|---|---|---|---|
| | | | | | | $C_4$ | $C_6$ | $C_8^+$ | |
| C1 | 80 | 20 | 3.9 | 120 | 1657 | 91.2 | 7.9 | 0.9 | 95.2 |
| C2 | 40 | 20 | 7.1 | 90 | 4035 | 93.0 | 6.5 | 0.5 | 99.6 |
| C2 | 40 | 100 | 22.5 | 90 | 2551 | 93.7 | 5.9 | 0.4 | 99.2 |

[a]Percentage by weight determined by GC (percentage by weight of $C_4$, $C_6$ and $C_8^+$ cuts with respect to all of the oligomers).
[b]Percentage by weight of 1-butene in the $C_4$ cut.

The above examples demonstrate that the complexes of the invention exhibit good activity in the oligomerization of ethylene.

may or may not contain heteroelements, and aromatic groups which may or may not be substituted and which may or may not contain heteroelements, the group R² is selected from alkyl groups which may or may not be cyclic, which may or may not be substituted and which may or may not contain heteroelements, and aromatic groups which may or may not be substituted and which may or may not contain heteroelements, with the condition that when a precursor of nickel with an oxidation number of (+II) is in the composition, it is in the presence of a reducing agent or in the presence of a Brönsted base.

2. The composition according to claim 1, comprising an additional Lewis base.

3. The composition according to claim 2, in which the additional Lewis base is a phosphine of the type P(A¹R'¹ᵃ) (A''¹R'¹ᵇ)(A'''¹R'¹ᶜ) or a phosphinamine of the type (R'¹ᵃA¹)(R'¹ᵇA¹)P—NH(R'²) or (R'¹ᵃA¹)(R'¹ᵇA¹)P—NH—S(O)₂(R'²) in which:

A¹, A''¹ and A'''¹, which may be identical or different, are independently O, S, NR³ or a single bond between the phosphorus atom and a carbon atom, the group R³ is either a hydrogen atom or an alkyl group, which may or may not be cyclic, which may or may not be substituted and which may or may not contain heteroelements, or an aromatic group which may or may not be substituted and which may or may not contain heteroelements, the groups R'¹ᵃ, R'¹ᵇ and R'¹ᶜ, being mutually identical or different and which may or may not be bonded together, are selected from alkyl groups which may or may not be cyclic, which may or may not be substituted and which may or may not contain heteroelements, and aromatic groups which may or may not be substituted and which may or may not contain heteroelements, the group R'² is selected from alkyl groups which may or may not be cyclic, which may or may not be substituted and which may or may not contain heteroelements, and aromatic groups which may or may not be substituted and which may or may not contain heteroelements.

4. The composition according to claim 1, in which the groups R¹ᵃ and R¹ᵇ, which may be identical or different and which may or may not be bonded together, and the groups R'¹ᵃ, R'¹ᵇ and R'¹ᶜ, which may be indentical or difference and which may or may not be bonded together, are independently selected from alkyl groups containing 1 to 15 carbon atoms and aromatic groups containing 5 to 20 carbon atoms, which may or may not be substituted and which may or may not contain heteroelements.

5. The composition according to claim 1, in which the groups R¹ᵃ and R¹ᵇ which may be identical or different, which may or may not be bonded together, and the groups R'¹, i.e. R'¹ᵃ, R'¹ᵇ and R'¹ᶜ which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl) phenyl, benzyl, naphthyl, bisnaphthyl, pyridyl, bisphenyl, furanyl and thiophenyl groups, which may or may not be substituted and which may or may not contain heteroelements.

6. The composition according to claim 3, in which the groups R² and the groups R'², which may be identical or different, are independently selected from alkyl groups containing 1 to 15 carbon atoms and aromatic groups containing 5 to 20 carbon atoms, which may or may not be substituted and which may or may not contain heteroelements.

7. The composition according to claim 3, in which the groups R² and the groups R'², which may be identical or different, are independently selected from methyl, trifluoromethyl, ethyl, n-propyl, i-propyl, n-butyl, i-butyl, t-butyl, pentyl, cyclohexyl and adamantyl groups, which may or may not be substituted and which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not be substituted and which may or may not contain hetero elements.

8. The composition according to claim 1, in which the nickel precursor with oxidation number (0) is selected from nickel(0)bis(cycloocta-1,5-diene), nickel(0)bis(cycloocta-1,3-diene), nickel(0)bis(cyclooctatetraene), nickel(0)bis(cycloocta-1,3,7-triene), bis(o-tolylphosphito) nickel(0) (ethylene), nickel(0)tetrakis(triphenylphosphite), nickel(0)tetrakis (triphenylphosphine) and nickel (0)bis(ethylene), alone or as a mixture thereof.

9. The composition according to claim 1, in which the nickel precursor with oxidation number (+II) is selected from nickel (II) chloride, nickel(dimethoxyethane) chloride(II), nickel(II) bromide, nickel(II)(dimethoxyethane) bromide, nickel((II)) fluoride, nickel(II) iodide, nickel((II)) sulphate, nickel((II)) carbonate, nickel((II))dimethylglyoxime, nickel ((II)) hydroxide, nickel((II)) hydroxyacetate, nickel(II) oxalate, nickel((II)) carboxylates, 2-ethylhexanoate, nickel ((II)) phenates, nickel((II)) acetate, nickel(II) trifluoroacetate, nickel((II))triflate, nickel(II) acetylacetonate, nickel ((II)) hexafluoroacetylacetonate, allylnickel(II) chloride, allylnickel(II) bromide, methallylnickel(II) chloride dimer, allylnickel(II) hexafluorophosphate, methallylnickel(II) hexafluorophosphate, biscyclopentadienyl nickel(II), bisallyl nickel(II) and bismethallyl nickel(II); in their hydrated or non-hydrated form, alone or as a mixture thereof.

10. The composition according to claim 1, further comprising an activating agent selected from the group consisting of tris(hydrocarbyl)aluminium compounds, chlorine-containing or bromine-containing hydrocarbylaluminium compounds, aluminoxanes, organo-boron compounds, and organic compounds which are capable of donating or accepting a proton, alone or as a mixture thereof.

11. The composition according to claim 1, in which the molar ratio between the ligand and the nickel precursor is in the range of 0.05 to 10.

12. A catalyst comprising a composition according to claim 1.

13. A process for oligomerizing an olefinic feed, comprising bringing said feed into contact with a composition according to claim 1.

14. The process according to claim 13, in which the feed comprises olefins containing 2 to 10 carbon atoms.

15. The process according to claim 13, in which the reaction is an ethylene oligomerization reaction.

16. The composition according to claim 1, in which the group R³ is either a hydrogen atom or an alkyl group, which may or may not be cyclic, which may not contain heteroelements, or an aromatic group, which may or may not contain heteroelements, the groups $R^{1a}$ and $R^{1b}$ being mutually identical or different and which may or may not be bonded together, are selected from alkyl groups which may or may not be cyclic, which may or may not contain heteroelements, and aromatic groups which may or may not contain heteroelements, the group $R^2$ is selected from alkyl groups which may or may not be cyclic, which may or may not contain heteroelements, and aromatic groups which may or may not contain heteroelements.

17. The composition according to claim 2, in which the additional Lewis base is a phosphine of the type $P(A^1R'^{1a})(A''^1R'^{1c})$ or a phosphinamine of the type $(R'^{1a}A^1)(R'^{1b}A^1)P\text{-}NH(R'^2)$ or $(R'^{1a}A^1))(R'^{1b}A^1)P\text{-}NH\text{-}S(O)_2(R'^2)$ in which:

$A^1$, $A'^1$ and $A''^1$, which may be identical or different, are independently O, S, $NR^3$ or a single bond between the phosphorus atom and a carbon atom, the group $R^3$ is either a hydrogen atom or an alkyl group, which may or may not be cyclic, which may or may not contain heteroelements, or an aromatic group which may or may not contain heteroelements, the groups $R'^{1a}$, $R'^{1b}$ and $R'^{1c}$, being mutually identical or different and which may or may not be bonded together, are selected from alkyl groups which may or may not be cyclic, which may or may not contain heteroelements, and aromatic groups which may or may not contain heteroelements, the group $R'^2$ is selected from alkyl groups which may or may not be cyclic, which may or may not contain heteroelements, and aromatic groups which may or may not contain heteroelements.

18. The composition according to claim 1, in which the groups $R^{1a}$ and $R^{1b}$, which may be identical or different and which may or may not be bonded together, and the groups $R'^{1a}$, $R'^{1b}$ and $R'^{1c}$, which may be identical or different and which may or may not be bonded together, are independently selected from alkyl groups containing 1 to 15 carbon atoms and aromatic groups containing 5 to 20 carbon atoms, which may or may not contain heteroelements.

19. The composition according to claim 3, in which the groups $R^2$ and the groups $R'^2$, which may be identical or different, are independently selected from alkyl groups containing 1 to 15 carbon atoms and aromatic groups containing 5 to 20 carbon atoms, which may or may not contain heteroelements.

20. The composition according to claim 3, in which the groups $R^2$ and the groups $R'^2$, which may be identical or different, are independently selected from methyl, trifluoromethyl, ethyl, n-propyl, i-propyl, n-butyl, i-butyl, t-butyl, pentyl, cyclohexyl and adamantyl groups, which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-ditert-butyl-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, which may or may not contain heteroelements; and in which the groups $R^{1a}$ and $R^{1b}$ which may be identical or different, which may or may not be bonded together, and the groups $R'^{1a}$, $R'^{1b}$ and $R'^{1c}$ which may be identical or different, which may or may not be bonded together, are independently selected from methyl, trifluoromethyl, ethyl, n-propyl, i-propyl, n-butyl, i-butyl, t-butyl, pentyl, cyclohexyl and adamantyl groups which may or may not contain heteroelements; and from phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl groups, which may or may not contain heteroelements.

* * * * *